United States Patent [19]

Jautelat et al.

[11] Patent Number: 4,495,370
[45] Date of Patent: Jan. 22, 1985

[54] PREPARATION OF 5-ARYLOXY-1-CHLORO-3,3-DIMETHYL-2-PENTANONES

[75] Inventors: Manfred Jautelat, Burscheid; Dieter Arlt, Cologne; Gerhard Jäger, Leverkusen, all of Fed. Rep. of Germany

[73] Assignee: Bayer Aktiengesellschaft, Leverkusen, Fed. Rep. of Germany

[21] Appl. No.: 498,611

[22] Filed: May 27, 1983

[30] Foreign Application Priority Data

Jun. 12, 1982 [DE] Fed. Rep. of Germany ....... 3222221

[51] Int. Cl.³ .............................................. C07C 45/42
[52] U.S. Cl. .................................... 568/322; 568/645; 568/655; 568/306; 568/43; 568/45; 568/47; 568/586; 260/465 D; 564/440; 564/441; 560/53
[58] Field of Search ............... 568/322, 645, 655, 306, 568/43, 45, 47, 586; 260/465 D; 564/440, 441; 560/53

[56] References Cited

U.S. PATENT DOCUMENTS 3,322,813 5/1967 Seki et al. ............................. 568/655
3,926,989 12/1975 Rebsdat et al. ...................... 568/655
4,399,309 8/1983 Jaulelat et al. ...................... 568/322

Primary Examiner—James H. Reamer
Attorney, Agent, or Firm—Sprung Horn Kramer & Woods

[57] ABSTRACT

A process for the preparation of a 5-aryloxy-1-chloro-3,3-dimethyl-2-pentanone of the formula

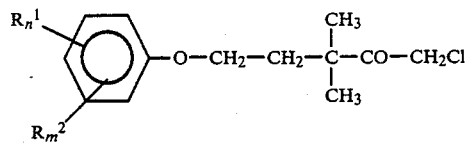

in which $R^1$ and $R^2$ each independently is halogen, alkyl having 1 to 4 carbon atoms, alkoxy or alkylthio each having 1 to 2 carbon atoms, halogenoalkyl, halogenoalkoxy or halogenoalkylthio each having 1 to 2 carbon atoms and 1 to 5 halogen atoms, cyclohexyl, dialkylamino having 1 to 4 carbon atoms in each alkyl moiety, nitro, cyano, alkoxy-carbonyl having 1 to 4 carbon atoms in the alkyl moiety, phenyl or halophenyl, m and n each independently is an integer from 0 to 5, and $m+n \leq 5$, comprising reacting 1,1,5-trichloro-3,3-dimethyl-1-pentene of the formula

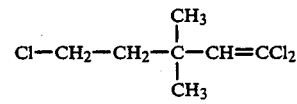

with a phenol of the formula

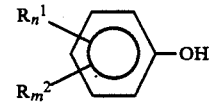

in the presence of a base in a diluent, to produce a compound of the formula

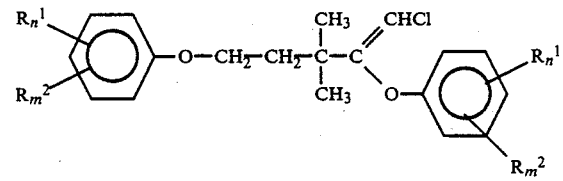

and subjecting such reaction product to acid hydrolysis.

6 Claims, No Drawings

PREPARATION OF 5-ARYLOXY-1-CHLORO-3,3-DIMETHYL-2-PENTANONES

The present invention relates to a new process for the preparation of 5-aryloxy-1-chloro-3,3-dimethyl-2-pentanones, some of which are known, which can be used as intermediate products for the synthesis of azole derivatives having fungicidal activity.

It has already been disclosed that chloromethyl ketones are obtained selectively from 1,1-dichloro-1-alkenes by reaction with phenolates and acid hydrolysis (U.S. application Ser. No. 329,959, filed Dec. 30, 1981, now pending). This process can be widely used and its principal restriction is in the availability of the 1,1-dichloro-1-alkenes. 1,1-Dichloro-1-alkenes are prepared by reaction of suitable alkyl chlorides and vinylidene chloride (J.Am.Chem.Soc. 74, 2885 (1952)). The starting materials necessary for the preparation of 5-aryloxy-1,1-dichloro-3,3-dimethyl-1-pentenes, the 4-aryloxy-2-chloro-2-methylbutanes are, however, only available with great difficulty. Thus, elimination to give olefins is found in the reaction of 2,4-dichloro-2-methylbutane with phenolates.

It has now been found that 5-aryloxy-1-chloro-3,3-dimethyl-2-pentanones of the formula

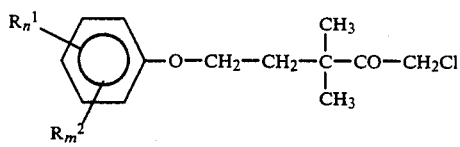

in which $R^1$ and $R^2$ are identical or different and represent halogen, alkyl having 1 to 4 carbon atoms, alkoxy and alkylthio, each having 1 to 2 carbon atoms, halogenoalkyl, halogenoalkoxy and halogenoalkylthio, each having 1 to 2 carbon atoms and 1 to 5 identical or different halogen atoms, or represent cyclohexyl, dialkylamino having 1 to 4 carbon atoms in each alkyl moiety, and also represent nitro, cyano and alkoxycarbonyl having 1 to 4 carbon atoms in the alkyl moiety and phenyl which is optionally substituted by halogen, and n and m are identical or different and represent the numbers 0, 1, 2, 3, 4 or 5, with the proviso that the sum of n and m is not greater than 5,
are obtained when 1,1,5-trichloro-3,3-dimethyl-1-pentene of the formula

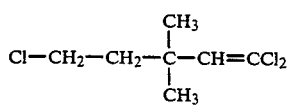

is reacted with phenols of the formula

in which $R^1$, $R^2$, n and m have the above meanings, in the presence of a base in a diluent, to give compounds of the formula

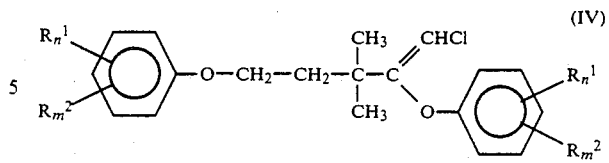

in which $R^1$, $R^2$, n and m have the above meanings, and this reaction product is subjected to acid hydrolysis.

Since it is known that the reaction of 1,1,5-trichloro-3,3-dimethyl-1-pentene (II) with alcoholates involves elimination to lead to 3,3-dimethyl-4-pentenoic acid derivatives (U.S. application Ser. No. 281,614, filed July 9, 1981, pending), it is extremely surprising that by the process according to the invention, with phenols of the formula (III) in the presence of a base, substitution, not elimination, takes place to give 5-aryloxy derivatives of the formula (IV).

The process according to the invention has a number of advantages. Thus, the starting material of the formula (II), 1,1,5-trichloro-3,3-dimethyl-1-pentene is readily available from isoprene, hydrogen chloride and vinylidene chloride. A large number of new diaryloxy compounds of the formula (IV) can be prepared with this central feed stock and various phenols. After acid hydrolysis of the diaryloxy compounds of the formula (IV), 5-aryloxy-1-chloro-3,3-dimethyl-2-pentanones (I) are available in good yield.

When, for example, 1,1,5-trichloro-3,3-dimethyl-1-pentene and 2,4-dichlorophenol are used as starting materials, the reaction can be represented by the following equation:

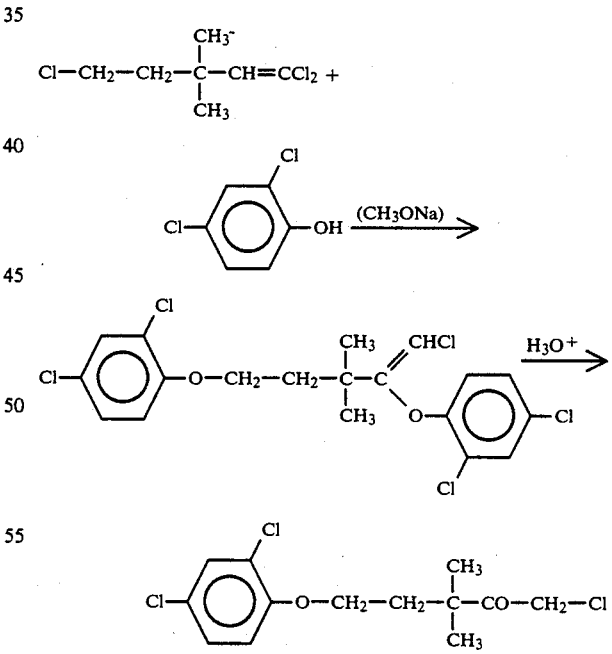

The 1,1,5-trichloro-3,3-dimethyl-1-pentene used as starting material is unambiguously designated by the formula (II). The compound and its preparation are known (compare in this context U.S. application Ser. No. 281,614 and details above).

The phenols which are also to be used according to the invention are generally defined by formula (III). In this formula, $R^1$ and $R^2$ preferably represent halogen, or represent alkyl, alkoxy and alkylthio, each having 1 to 2 carbon atoms, or represent halogenoalkyl, halogenoalkoxy and halogenoalkylthio having 1 to 2 carbon and 1 to 5 fluorine or chlorine atoms, or represent cyclohexyl, dialkylamino having 1 to 2 carbon atoms in the alkyl moieties, or represent nitro and cyano, and also represent alkoxycarbonyl having 1 to 2 carbon atoms in the alkyl moiety and represent phenyl, which is optionally substituted once to three times by chlorine or fluorine, and the indices n and m preferably represent the figures 0, 1 and 2.

The phenols of the formula (III) are known compounds customary in laboratories. Examples which may be mentioned are: phenol, 2-chlorophenol, 4-chlorophenol, 3-chlorophenol, 2,4-dichlorophenol, 2,5-dichlorophenol, 2,6-dichlorophenol, 2,4,5-trichlorophenol, 2,4,6-trichlorophenol, pentachlorophenol, 2-nitrophenol, 4-nitrophenol, 3-nitrophenol, 4-chloro-2-nitrophenol, 3-chloro-4-nitrophenol, 2,4-dichloro-5-nitrophenol, 2-methylphenol, 3-methylphenol, 4-methylphenol, 4-chloro-2-methylphenol, 5-chloro-2-methylphenol, 2-methyl-5-nitrophenol, 4-chloro-3-methylphenol, 3-methyl-4-nitrophenol, 4-methyl-2-nitrophenol, 3,5-dimethylphenol, 4-tert.-butylphenol, 4-cyclohexylphenol, 4-phenylphenol, 4-fluorophenol, 2-fluorophenol, 2,4-difluorophenol, 2-chloro-4-fluorophenol, 4-trifluoromethylthio-phenol, 4-trifluoromethoxy-phenol, 3-trifluoromethyl-phenol, 2-chloro-4-trifluoromethyl-phenol and 4-cyanophenol.

Suitable diluents are all inert organic solvents. Polar solvents, in particular dimethylformamide, N-methylpyrrolidone, hexamethylphosphoric triamide, dimethyl sulphoxide, 1,3-dimethyl-2-imidazolidone, tetramethylurea, sulpholane, ethers, such as diethyl ether, dioxane or alcohols, such as glycol, diethylene glycol monoethyl ether or diethylene glycol monomethyl ether, amongst others, are preferably used.

The reaction of the 1,1,5-trichloro-3,3-dimethyl-1-pentene (II) with phenols is carried out in the presence of bases. Suitable as such are alkali metal and alkaline earth metal hydroxides, such as sodium hydroxide, potassium hydroxide or calcium hydroxide, alkali metal and alkaline earth metal carbonates, such as potassium carbonate or sodium carbonate and alkali metal alcoholates, such as sodium methoxide, sodium ethoxide, sodium butoxide and potassium tert.-butoxide.

During the reaction of the compound of the formula (II) with the phenols of the formula (III), the reaction temperature can be varied within a wide range. In general, it is carried out between +100° and 250° C., preferably between 120° and 220° C. The reaction can be carried out both under normal pressure in an open system and under pressure in an autoclave in the range of pressure between 1 and 50 bar.

In carrying out the process according to the invention, 2 to 4 equivalents, preferably 2 to 3, of the phenol of the formula (III) are reacted with 2 to 4 equivalents of base, preferably 2 to 3, and with one equivalent of 1,1,5-trichloro-3,3-dimethyl-1-pentene (II) to give (IV).

The subsequent hydrolysis is carried out with mineral acids, preferably sulphuric acid or hydrochloric acid, and/or with organic acids, such as formic acid, trifluoroacetic acid, oxalic acid, p-toluenesulphonic acid or methanesulphonic acid at temperatures from +20° to 150° C., preferably at 40° to 100° C. Suitable solvents for the hydrolysis are alcohols, such as ethanol or methanol, ketones, such as acetone, or ethers, such as dioxane. In general, the acids are employed in excess. They can also be present diluted in water.

According to a particular embodiment, the process can be such that initially the 1,1,5-trichloro-3,3-dimethyl-1-pentene of the formula (II) is reacted with only one equivalent of a phenol of the formula (III) in the presence of a base, to give a compound of the formula

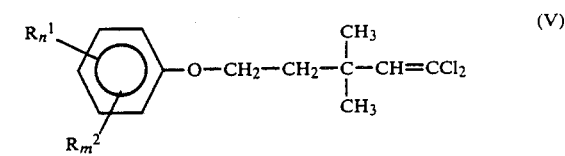

in which $R^1$, $R^2$, n and m have the above meanings, and, in an additional step, is brought to reaction with a phenolate of the formula

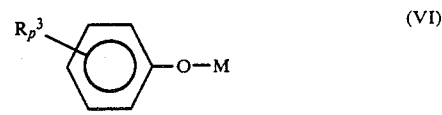

in which
$R^3$ represents halogen and represents alkyl having 1 to 2 carbon atoms,
p represents the figures 0, 1, 2 or 3, and
M represents one equivalent of an alkali metal or alkaline earth metal ion,
thus obtaining compounds of the formula

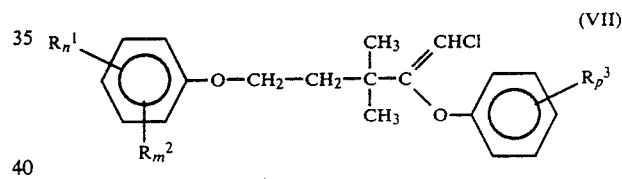

in which $R^1$, $R^2$, $R^3$, n, m and p have the meanings indicated previously,
which are then subjected to acid hydrolysis according to the process, compounds of the formula (I) being obtained. This process variant is particularly advantageous when the phenols of the formula (II) are costly or available with difficulty; the phenolates of the formula (VI) then selected for the purpose will be compounds readily available a large scale.

Another particular embodiment comprises uniting in a one-pot process the reactions, (a) of 1,1,5-trichloro-3,3-dimethyl-1-pentene of the formula (II) with a phenol of the formula (III) and (b) the hydrolysis of the compounds of the formula (IV), which are usually separate.

The compounds of the formula (I) are interesting intermediate products; some of them are known (U.S. Ser. No. 329,959, supra). By reacting them with azoles of the formula

in which A represents nitrogen or the CH group, in the presence of an acid-binding agent and a diluent, compounds of the formula

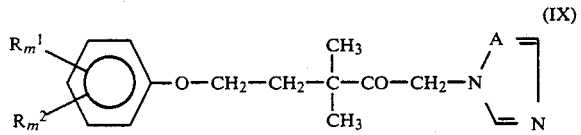

in which $R^1$, $R^2$, n, m and A have the meanings indicated above,
are obtained, which can be reacted with propargyl halides in the presence of activated aluminum to give hydroxyalkyl-azolyl derivatives of the formula

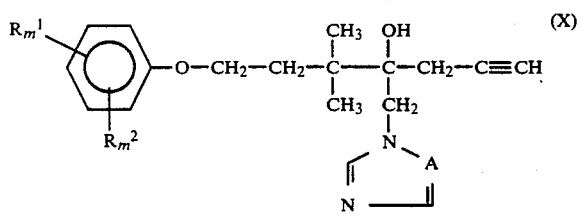

in which $R^1$, $R^2$, n, m and A have the meanings indicated above.

The compounds have fungicidal activity.

PREPARATION EXAMPLES

EXAMPLE 1

1st Step

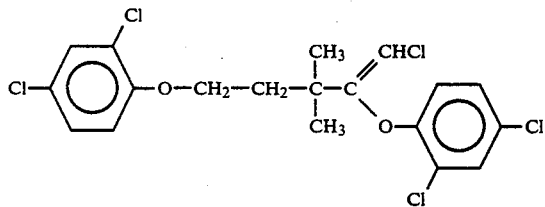

489 g (3 mols) of 2,4-dichlorophenol are dissolved in 1.2 liters of N-methylpyrrolidone, and 600 ml (3 mols) of a 30% strength solution of sodium methylate are added. Methanol and 200 ml of N-methylpyrrolidone are distilled off at 20 mbar. 201 g (1 mol) of 1,1,5-trichloro-3,3-dimethyl-1-pentene are slowly added dropwise at 200° C. and under atmospheric pressure. The mixture is stirred for a further 6 hours at 200° C. The cooled solution is diluted with methylene chloride and extracted by shaking several times with dilute sodium hydroxide solution. The dried solution is freed of solvent on a rotary evaporator at 0.1 mbar and 150° C. 410 g (0.9 mol; 90% of theory) of 1-chloro-3,3-dimethyl-2,5-di-(2,4-dichlorophenoxy)-1-pentene remain as an oil.

NMR (CDCl$_3$): δ=1.2 (s, 6H), 2.1 (t, 2H, J=7 Hz), 4,1 (t, 2H, J=7 Hz), 5.95 (s, 1H), 6.75–7.4 (m, 6H).

2nd Step

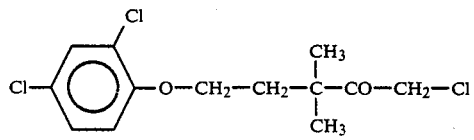

454 g (1 mol) of 1-chloro-3,3-dimethyl-2,5-di-(2,4-dichlorophenoxy)-1-pentene in 500 ml of formic acid and 50 ml of concentrated hydrochloric acid are heated at 100° C. for 9 hours. The mixture is diluted with methylene chloride and extracted by shaking once with water and three times with dilute sodium hydroxide solution. After drying the solution, the solvent is distilled off in vacuo. 238 g (0.77 mol; 77% of theory) of 5-(2,4-dichlorophenoxy)-1-chloro-3,3-dimethyl-2-pentanone remain, which slowly crystallize. After washing with petroleum ether, the melting point is 55°–58° C.

EXAMPLE 2

1st Step

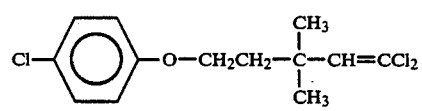

128 g (1 mol) of 4-chlorophenol, 201 g (1 mol) of 1,1,5-trichloro-3,3-dimethyl-1-pentene (II) and 138 g (1 mol) of potassium carbonate in 1 liter of diethylene glycol dimethyl ether are heated under reflux for 10 hours. The mixture is then diluted with methylene chloride and extracted by shaking several times with water. The organic phase is freed of solvent on a rotary evaporator and then distilled at a boiling point of 135°–140° C./0.1 mbar. 252 g (0.86 mol, which is 86% of theory) of 5-(4-chlorophenoxy)-1,1-dichloro-3,3-dimethyl-1-pentene are obtained.

NMR (CDCl$_3$): δ=1.2 (s, 6H), 1.95 (t, 2H, J=7 Hz), 4.0 (t, 2H, J=7 Hz) 6.0 (s, 1H), 6.75–7.25 ppm (m, 4H).

2nd Step

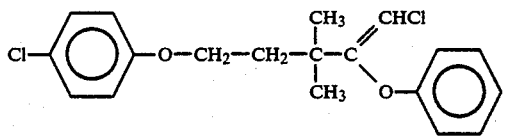

116 g (1 mol) of sodium phenolate and 147 g (0.5 mol) of 5-(4-chlorophenoxy)-1,1-dichloro-3,3-dimethyl-1-pentene in 500 ml of dimethylformamide are heated under reflux for 10 hours. The mixture is diluted with methylene chloride and extracted by shaking with 2N sodium hydroxide solution. The dried organic phase is freed of solvent in a rotary evaporator at 0.1 mbar and 150° C. 158 g (0.45 mol); 90% of theory) of 1-chloro-5-(4-chlorophenoxy)-3,3-dimethyl-2-phenoxy-1-pentene remain as an oil.

NMR (CDCl$_3$): δ=1.2 (s, 6H), 2.0 (t, 2H, J=7 Hz), 4.0 (t, 2H, J=7 Hz), 5.9 (s, 1H), 6.7–7.4 ppm (m, 9H).

3rd Step

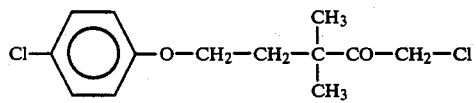

351 g (1 mol) of 1-chloro-5-(4-chlorophenoxy)-3,3-dimethyl-2-phenoxy-1-pentene in 600 ml of ethanol and 200 ml of concentrated hydrochloric acid are heated under reflux for 4 hours. The alcohol is distilled off in vacuo, and the residue is diluted with methylene chloride and extracted by shaking once with water and three times with dilute sodium hydroxide solution. The dried solution is freed of remaining solvent in vacuo. 239 g (0.89 mol, 89% of theory) of 1-chloro-5-(4-chlorophenoxy)-3,3-dimethyl-2-pentanone remain as an oil.

NMR (CDCl$_3$): δ=1.25 (s, 6H), 2.1 (t, 2H, J=6 Hz) 3.9 (t, 2H, J=6 Hz), 4.45 (s, 2H), 6.7–7.3 ppm (m, 4H).

It will be appreciated that the instant specification and examples are set forth by way of illustration and not limitation, and that various modifications and changes may be made without departing from the spirit and scope of the present invention.

What is claimed is:

1. A process for the preparation of a 5-aryloxy-1-chloro-3,3-dimethyl-2-pentanone of the formula

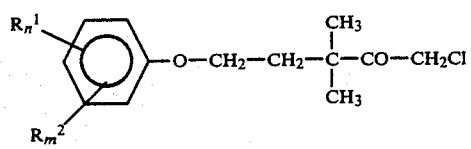

in which R$^1$ and R$^2$ each independently is halogen, alkyl having 1 to 4 carbon atoms, alkoxy or alkylthio each having 1 to 2 carbon atoms, halogenoalkyl, halogenoalkoxy or halogenoalkylthio each having 1 to 2 carbon atoms and 1 to 5 halogen atoms cyclohexyl, dialkylamino having 1 to 4 carbon atoms in each alkyl moiety, nitro, cyano, alkoxy-carbonyl having 1 to 4 carbon atoms in the alkyl moiety, phenyl or halophenyl, m and n each independently is an integer from 0 to 5, and m+n≦5, comprising reacting one equivalent of 1,1,5-trichloro-3,3-dimethyl-1-pentene of the formula

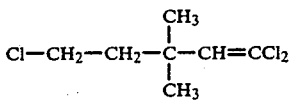

with 2 to 4 equivalents of a phenol of the formula

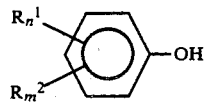

at a temperature between about 100° and 250° C. in the presence of 2 to 4 equivalents of a base in a diluent, to produce a compound of the formula

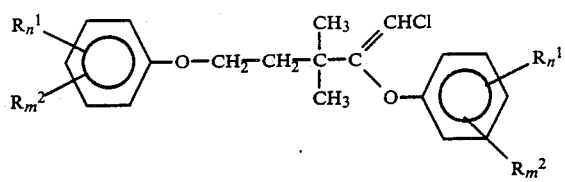

and subjecting such reaction product to acid hydrolysis with the aid of a mineral acid at a temperature between about 20° and 150° C.

2. A process according to claim 1 wherein the base is an alkali metal or alkaline earth metal hydroxide or carbonate, or an alkali metal alcoholate.

3. A process according to claim 1, wherein the reaction with the phenol is carried out at a temperature between about 120° and 220° C., and the subsequent hydrolysis is carried out at a temperature between about 40° and 100° C.

4. A process according to claim 1, wherein the hydrolysis is carried out with a mixture of a mineral acid and an organic acid.

5. A process according to claim 1, wherein the reaction of the 1,1,5-trichloro-3,3-dimethyl-1-pentene with the phenol and the subsequent hydrolysis are carried out in a one-pot process without intermediate isolation.

6. A process according to claim 1, wherein the 1,1,5-trichloro-3,3-dimethyl-1-pentene is initially reacted with one equivalent of the phenol in the presence of a base to give a compound of the formula

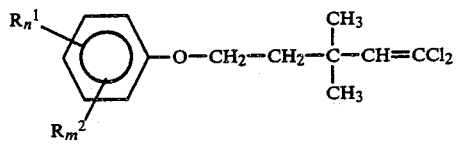

which, in an additional step, is reacted with a phenolate of the formula

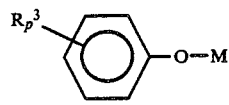

in which
R$^3$ is halogen or alkyl having 1 or 2 carbon atoms,
p is an integer from 0 to 3, and
M is one equivalent of an alkali metal or alkaline earth metal ion,
to produce a compound of the formula

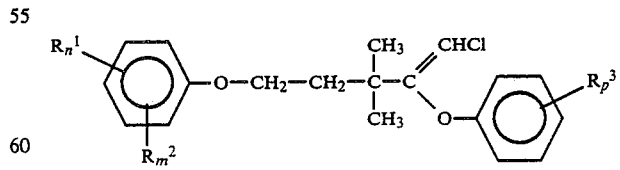

which is subjected to the acid hydrolysis.

* * * * *